(12) United States Patent
Chiang (10) Patent No.: US 6,191,850 B1
(45) Date of Patent: Feb. 20, 2001

(54) SYSTEM AND METHOD FOR INSPECTING AN OBJECT USING STRUCTURED ILLUMINATION

(75) Inventor: Gilbert W. J. Chiang, San Francisco, CA (US)

(73) Assignee: Cognex Corporation, Natick, MA (US)

(*) Notice: Under 35 U.S.C. 154(b), the term of this patent shall be extended for 0 days.

(21) Appl. No.: 09/418,643

(22) Filed: Oct. 15, 1999

(51) Int. Cl.[7] ....................................... G01N 21/00
(52) U.S. Cl. ............................ 356/237.4; 356/237.1; 356/237.2; 356/237.3
(58) Field of Search ......................... 356/237.1, 237.2, 356/237.3, 237.4; 250/201.4

(56) References Cited

U.S. PATENT DOCUMENTS 5,003,166 * 3/1991 Girod ................................ 250/201.4
5,841,530 * 11/1998 Hewitt et al. ....................... 356/237

* cited by examiner

*Primary Examiner*—Frank G. Font
*Assistant Examiner*—Roy M. Punnoose
(74) *Attorney, Agent, or Firm*—William A. Loginov; Russ Weinzimmer (57) ABSTRACT

A system and method for inspecting the surface of an object using structured illumination is provided. A structured illuminator having a diffuser assembly, grid pattern and beam splitter projects the grid pattern on the surface. The projected grid pattern is viewed by a camera, which is aligned on-axis with the projection and substantially perpendicular to the surface. The structured grid pattern makes more-pronounced any surface defects. The projected image, defined by the grid pattern and received by the camera, is analyzed using a two-step technique that, first locates and scores the individual features of the grid, and then compares the locations of the actual features as viewed, to ideal locations for such features.

13 Claims, 7 Drawing Sheets

SYSTEM AND METHOD FOR INSPECTING AN OBJECT USING STRUCTURED ILLUMINATION

FIELD OF THE INVENTION

This invention relates to machine vision systems for inspecting objects, and more particularly to systems that conduct surface inspection using structured illumination.

BACKGROUND OF THE INVENTION

It is often desirable to inspect generally flat uniform surfaces for defects. Surface inspection is used in a variety of industries. The inspection process can utilize automated machine vision techniques, manual inspection techniques, in which a human operator views objects through a remote camera, or a combination of manual and automated techniques.

By way of example, the production of laminated security cards, sometimes referred to as "Smart Cards," involves the placement of a radio frequency-generating material between two layers of plastic sheet laminate. The finished cards are used in a variety of readers in which the response of the card to a predetermined radio frequency signal, transmitted by the reader, uniquely identifies the cardholder. Because of the substantial heat and pressure used to produce such cards, they are susceptible to the formation of defects on their surfaces during manufacture. These defects, which cause problems during the printing process, may be difficult to detect during visual inspection by a human operator, or even by automated inspection. In particular, the so-called dimple defect, which exhibits a gradual waviness emanating from a point on the card surface may be quite difficult to detect, and will only show up when the card is printed upon. Other types of defects may be equally difficult to spot, particularly when viewed using a remote camera that displays the card on a monitor.

Visualization of these defects can be made simpler by the use of structured illumination, where a pattern of light and shadow projected upon the surface enhances the visibility of any defects present. An effective and reliable way to determine whether surface defects are unacceptable is to measure the structured illumination grid features against predetermined tolerance values. This generally entails the numerical quantification of the underlying defects. However, accurate and reliable translation of the visual quality of a defect into a quantitative value is often difficult to accomplish. It is, therefore, an object of this invention to provide a system and method and apparatus for quantitatively inspecting a surface for defects. This system and method should enable easier and more reliable inspection by automated machine vision systems.

SUMMARY OF THE INVENTION

This invention overcomes limitations of the prior art by providing a system and method for effectively analyzing a pattern produced on a surface using structured light to determine underlying defects in the surface.

Briefly stated, a structured light, in the form of a grid pattern, is projected onto an object surface with the individual grid elements or "features" appearing as shadow lines thereon. The projected grid is viewed by an on-axis camera that is operatively interconnected to a machine vision system that resides, typically, as software on a computer. The machine vision system conducts a two-step analysis of grid features that first compares derived scores for grid features against desired tolerances and then compares locations of grid features against a set of ideal grid feature locations. Only if the viewed grid passes both steps of the test is the surface deemed acceptable.

According to a preferred embodiment, a structured light-projecting element is positioned between a light source and the surface to be inspected. The projecting element includes a first diffuser through which light passes and a second diffuser having a desired grid pattern overlaid thereon. A beam splitter, typically in the form of a 45-degree half-mirror, reflects the projected grid pattern onto the surface. Light is reflected back from the surface with a grid pattern defined (in shadow) thereon, through the beam splitter and back toward the viewing camera along the camera axis to strike the camera lens. According to another embodiment, a collimator and polarizer can be located between the second diffuser and beam splitter, and a similar type (characteristic) of polarizer can be located at the camera lens.

The machine vision system, according to the preferred embodiment, is adapted to analyze the projection of the grid onto the surface as viewed by the camera. The projected grid is first located using, for example, a fiducial that is formed in relation to the grid, and that has a different appearance than the features of the grid for easier identification. Once the grid is located, the machine vision system uses pattern recognition to identify and score specific features of the grid. The results are used in a two-step process to analyze the grid. In the first analysis step, the scores are compared against tolerance limits. If all feature scores do not fall within these tolerance limits, then the surface is immediately rejected as defective without proceeding to the second analysis step. If tolerance limits are met in the first step, then the second step proceeds. The data derived by the machine vision software related to the grid features is ranked by row and column so as to create a mathematical array of feature locations. Based upon this array, an ideal grid is computed within the software, and the locations of the actual grid features are compared with the ideal grid locations. Deviations from the ideal locations are again matched against tolerance limits. If these limits are exceeded, then the surface is rejected, otherwise the surface is passed as acceptable.

BRIEF DESCRIPTION OF THE DRAWINGS

The foregoing and other objects and advantages of the invention will become more clear with reference to the following detailed description as illustrated by the drawings in which.

DETAILED DESCRIPTION OF AN ILLUSTRATIVE EMBODIMENT

Figure 1:
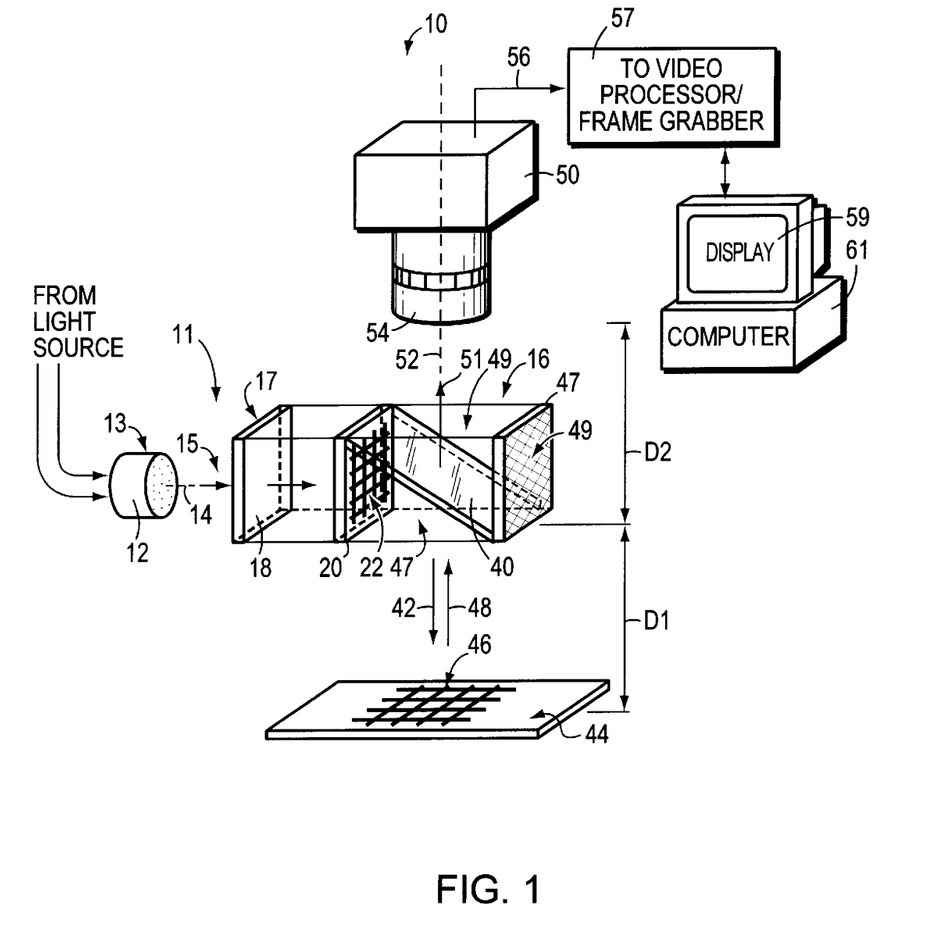
FIG. 1 is a somewhat schematic perspective view of an inspection system including details of a structured illuminator according to an embodiment of this invention.

FIG. 1 shows an inspection system 10 according to a preferred embodiment of this invention. An illumination assembly 11 for use with this system is now described. This illumination assembly includes a fiber optic cable 13 for transmitting light from a remote source having a high-intensity bulb (not shown) to an opposing cable tip 12. The tip 12 is arranged to project illumination light along a light source axis 14. While a cable is used according to this embodiment, the light can be fed to the assembly in a variety of ways. Typically, the preferred illumination light is generated by an illumination assembly that includes a remote, high-intensity lighting element (a halogen bulb not shown) optically connected to the fiber optic cable 13 at a remote cable end. However, light can also be delivered using mirrors and/or direct projection from a bulb (or light emitting diodes) with or without focusing lenses according to alternate embodiments of the invention. In a preferred embodiment, the illumination assembly can be based upon a Diffuse On-Axis Light (Model 2) (DOAL-2) available from Dolan-Jenner Industries of Lawrence, Mass.

The light assembly 11 is further arranged so that the illumination light from the cable tip 12 passes over an empty region 15 (a cavity in a larger framework, for example) into a projecting element 16 shown schematically as a rectangular box with a light-transmissive end wall 17 adjacent to the fiber optic tip 12. In general, the projecting element 16 is an empty cavity with appropriate openings for allowing light to pass in the particular manner to be described further below. The input end wall 17 of the projecting element 16 includes a first diffuser 18 through which the light initially passes. The first diffuser 18 can comprise a uniform translucent surface (frosted glass, for example) or any other acceptable diffuser that scatters light passed therethrough. The diffuse light then passes into a second diffuser 20 within the projecting element. The second diffuser generally has a translucent surface that is similar to that of the first diffuser 18. This second diffuser has formed thereon a grid pattern 22 according to an embodiment of this invention. The grid 22 is shown in further detail in FIG. 2. In general, it comprises a matrix of crossing vertical line elements 30 and horizontal line elements 32. The vertical line elements 30 have substantially uniform thickness T1 and are spaced at a substantially uniform spacing S1 from each other. Likewise, the horizontal elements 32 each have a substantial uniform thickness T2 and are spaced from each other at a substantially uniform spacing S2. The resulting square elements or features 35 of the grid are highly regular in both the x-axis (horizontal) and y-axis (vertical) dimensions.

Figure 3:
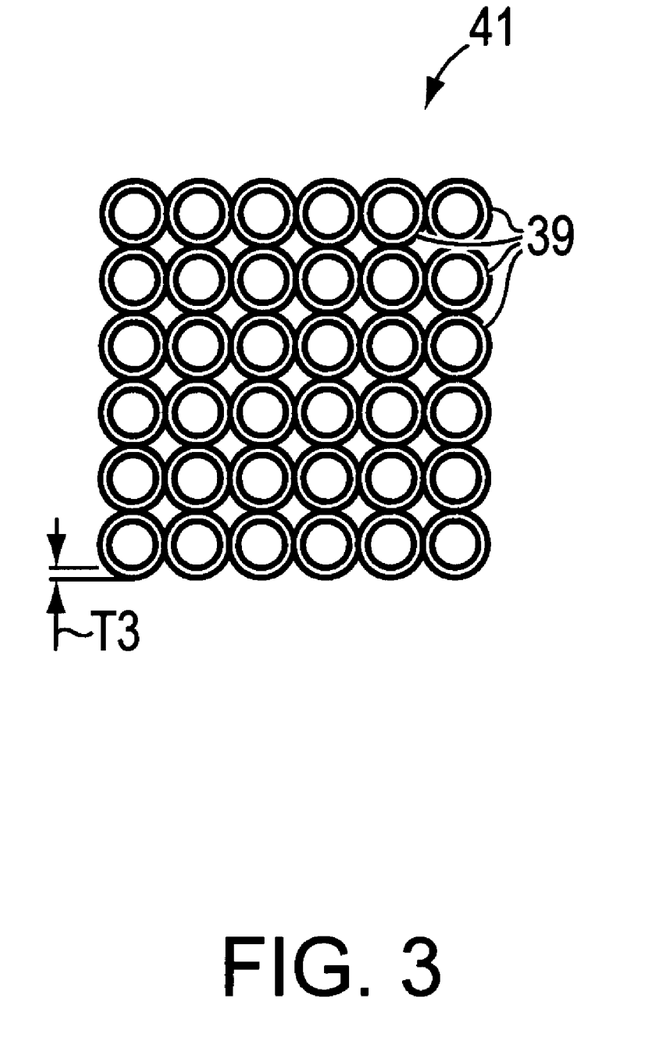
FIG. 3 is a plan view of a circular grid pattern according to an alternate embodiment of this invention.

In an alternate embodiment, the grid pattern can comprise another repeating, intersecting pattern of shapes. The particular grid elements shown in FIG. 3 are circles 39 that touch each other along the horizontal and vertical directions. This matrix of repeating, touching circles thereby forms a regular grid 41. Such a circular-feature grid can be preferable for detecting certain forms of defects, including the dimple defect. Accordingly, the term "grid" should be taken broadly to include any acceptable, repeating/intersecting pattern. Also, such a "grid" pattern should typically have a regular spacing and size of elements therein. However, it is contemplated that size and spacing of elements may vary according to alternate embodiments.

The desired grid pattern can be provided to a separate light-transmissive surface, or preferably formed directly on the second diffuser surface on the face that is more remote from the first diffuser and nearer to an angled half-mirror/beam splitter 40 (described below). The formation of the grid pattern either separately or on the second diffuser can, likewise, be accomplished in a variety of ways. The grid can be applied by screen-printing or similar printing processes using ink or paint. It can be etched onto the surface or can be overlaid as a printed sheet having dark grid elements laid onto a transparent material. The transmitted light passes through the second diffuser 20 onto the above-referenced half-mirror/beam splitter 40. The transmitted light has a defined set of shadows in the shape of the grid pattern 22. The half-mirror/beam splitter functions to transmit part of the passing light along the source axis 14 toward the far end wall 47 of the projecting element. The far end wall 47 is covered with a light-absorbing material 49 such as black velvet so that virtually all light striking this surface is not reflected back again. The other part of the light passed through the grid 22 is reflected from the half-mirror 40 at a right angle toward the surface 44 of an object to be inspected. This reflected light passes out of the projecting element 16 though an open bottom 47 (see arrow 42). The shadow lines formed in the light beam by the grid become a corresponding grid image 46 on the object surface 44.

It can be observed that any defects on the surface become significantly pronounced in the projected grid pattern when this pattern is viewed on-axis with the projected light. To this end, the surface light with its corresponding grid pattern is reflected back toward the projecting element (arrow 48), and a portion of this reflected surface light is, thus, transmitted back through the half-mirror. The passed light projects through an open top 49 in the projecting element 16 to reach a camera 50 (arrow 51). The light is aligned generally along an axis of alignment 52 with respect to the optical plane of the camera 50. To this end, the object surface is usually oriented perpendicular to the camera axis 52. Likewise, the grid illumination light strikes the surface perpendicularly, and is, accordingly, reflected back from the surface perpendicularly along the axis 52.

The camera 50, in this embodiment, can comprise any acceptable video camera such as a CCD element camera. An appropriate lens 54 is provided. The lens can be adjustable for focus, zoom, aperture, and a variety of other optical characteristics. According to a preferred embodiment, a 16 mm lens is used. The exact lens and camera specification is highly variable. Adjustment of lens optics can be accomplished manually during either set up or run time, or at selected times by an acceptable automated focusing mechanism (not shown). Data from the camera is transmitted via a line 56 to a video processor and/or frame grabber 57 for final viewing at a display 59. The display 59 can be a stand-alone monitor or the monitor of an underlying computer system 61 that enables automated machine vision processes to be performed using a variety of commercially software packages. Generally the display is a digital representation of the image defined by a matrix of underlying pixels representing a gray scale or color image. Gray scale is preferred according to this embodiment as generally better at distinguishing the image of the reflected grid pattern. The distance D1 between the illuminator and the surface, as well as the distance D2 between the illuminator and camera (and the overall distance D1 and D2 together) are chosen so that the camera views a relatively tight window around the grid. According to a preferred embodiment, the distance D1 is approximately 15 mm and the distance D2 is approximately 55 mm, placing the camera approximately 70 mm from the surface 44 of the object. The grid features generally have a thickness T1, T2 that is arranged to project a shadow on the surface that is similar in size, or smaller than, the smallest surface defect of concern. Likewise the "thickness" T3 of the circular feature grid (FIG. 3) should be defined similarly to that the rectilinear grid of FIG. 2—that is, so as to form a projected shadow the same size or smaller than the smallest surface defect to be of concern. The overall grid size should be such that a large defect causes distortion that does not encompass more than one or two grid elements so that the overall grid is still observable.

Figure 4:
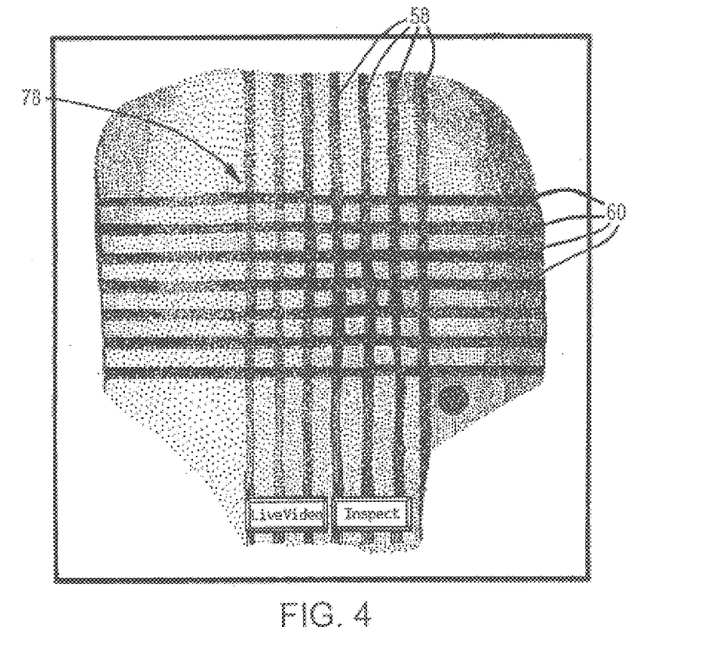
FIG. 4 is a plan view of a viewed image of a grid pattern on a normal surface according to this invention.
Figure 5:
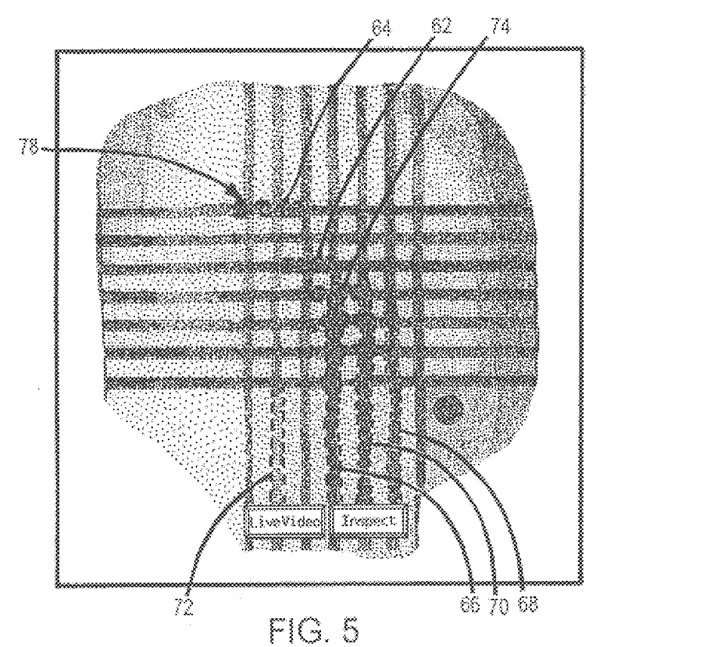
FIG. 5 is a plan view of a viewed image of a grid pattern on a defective surface according to this invention.

To this end, FIG. 4 shows a display of a grid pattern on a surface that is relatively free of defects. Projected vertical grid lines 58 and horizontal grid lines 60 appear relatively uniform and straight with little or no viewed waviness. Conversely, when viewing a defective surface, such as that shown in FIG. 5, various grid lines appear clearly distorted. Distorted line elements 62, 64, 66, 68, 70, 72 and 74 are clearly visible, for example. In this manner, a human operator and/or machine vision inspection system with apropriate video processing capabilities can more readily identify the underlying surface defects.

Figure 2:
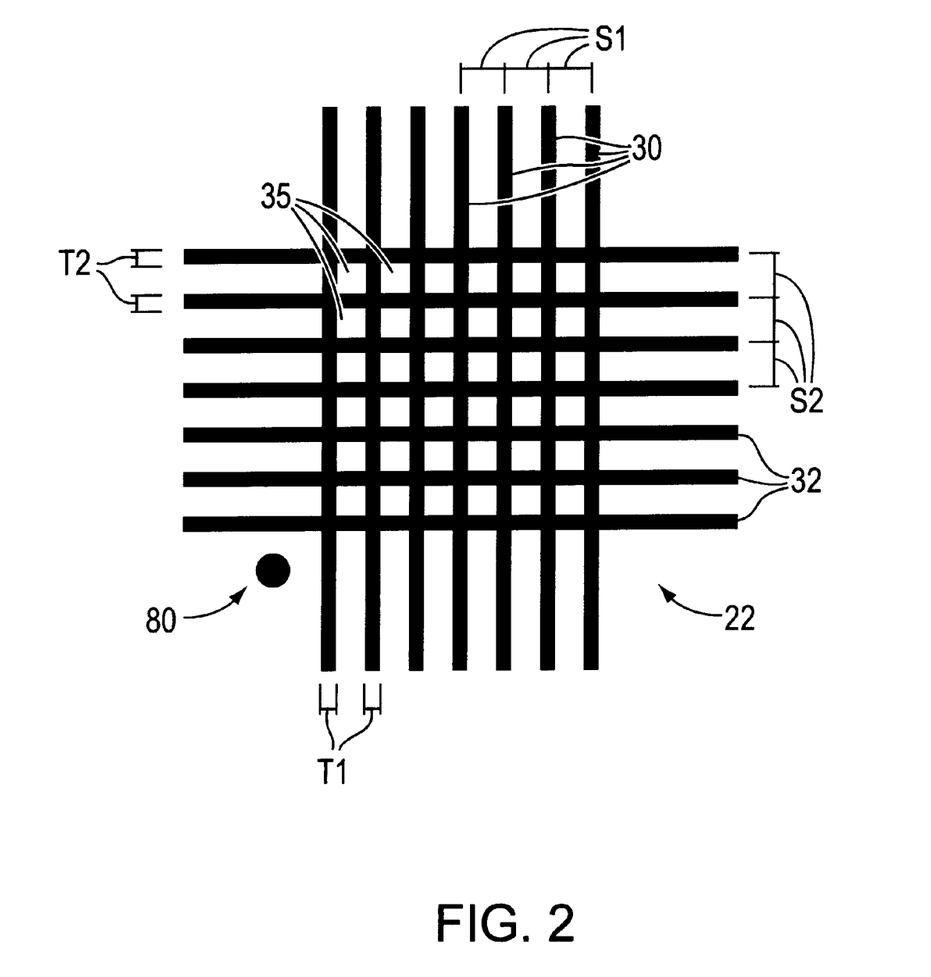
FIG. 2 is a plan view of a grid pattern for use with the illuminator of FIG. 1.

It should be noted that the grid pattern includes a fiducial 80 at one corner of the lattice. The fiducial becomes projected on the surface. In general, the fiducial should be a different geometry than that of the other grid elements so that it is easily identifiable. In this embodiment, where a series of lines defining square grid features are used, the fiducial is a dark circle. In particular, the fiducial can be used for basic grid alignment by a variety of manual and automated techniques described further below.

Figure 6:
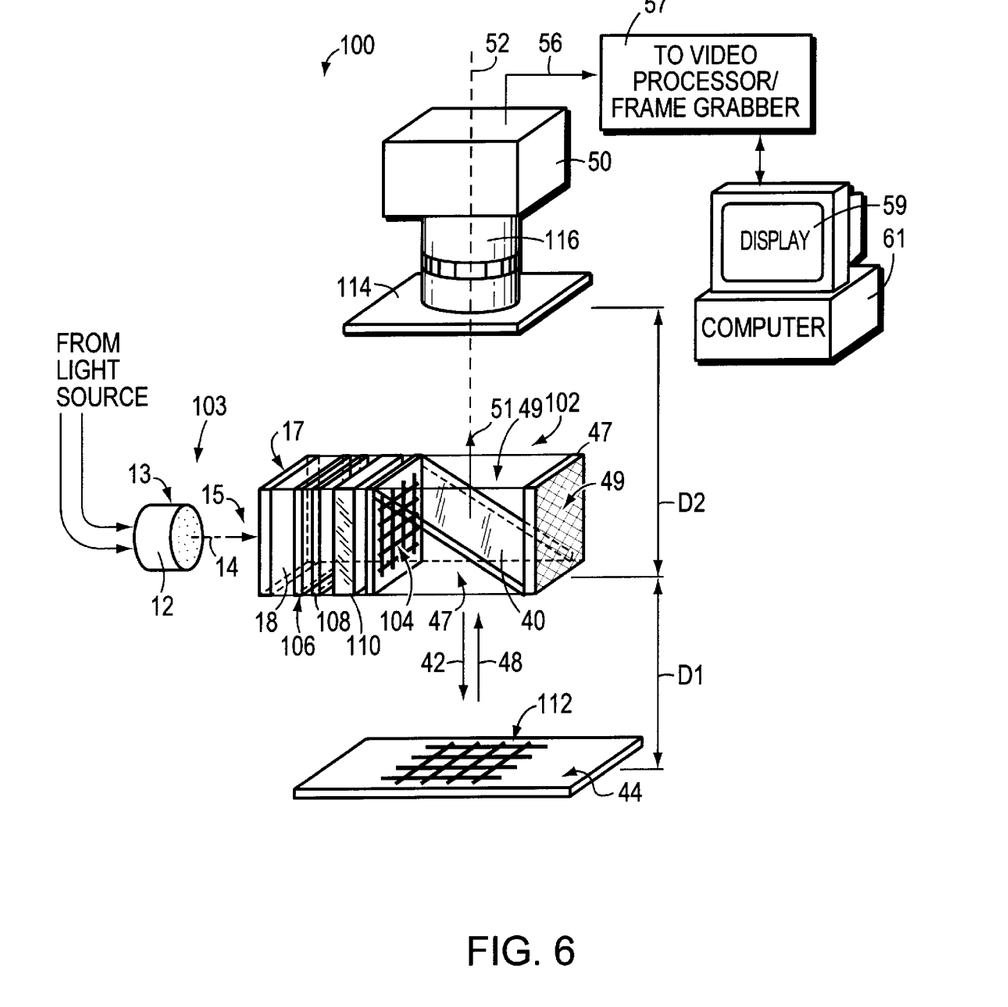
FIG. 6 is an inspection system including a structured illuminator according to an alternate embodiment of this invention.

A structured illuminator for the inspection system, according to an alternate embodiment, is shown in FIG. 6. The system 100 is arranged substantially similarly to the system 10 of FIG. 1. Accordingly, like elements throughout are given like reference numbers to those elements described in FIG. 1. With reference to FIG. 6, the projecting element 102 of the illumination assembly 103 differs from that of FIG. 1 in that its grid pattern 104 and its second diffuser 106 are separated by a conventional collimator 108 and polarizer 110. According to one embodiment, a plane polarizer is used. However, a variety of media having any of a variety of different polarizing characteristics can be employed according to alternate embodiments. As such, the image projected onto the surface 44 includes a projected grid pattern 112 that is defined based upon collimated, polarized light. The reflected image is viewed by the camera 50 through a corresponding polarizer 114 (also a plane polarizer in a preferred embodiment) using the lens 116. The lens 116 can particularly comprise a telecentric lens of conventional design. A telecentric lens is arranged to view light received generally parallel to the camera axis 52. According to an alternate embodiment the light source can comprise a monochromatic light source for improved image quality.

Figure 7:
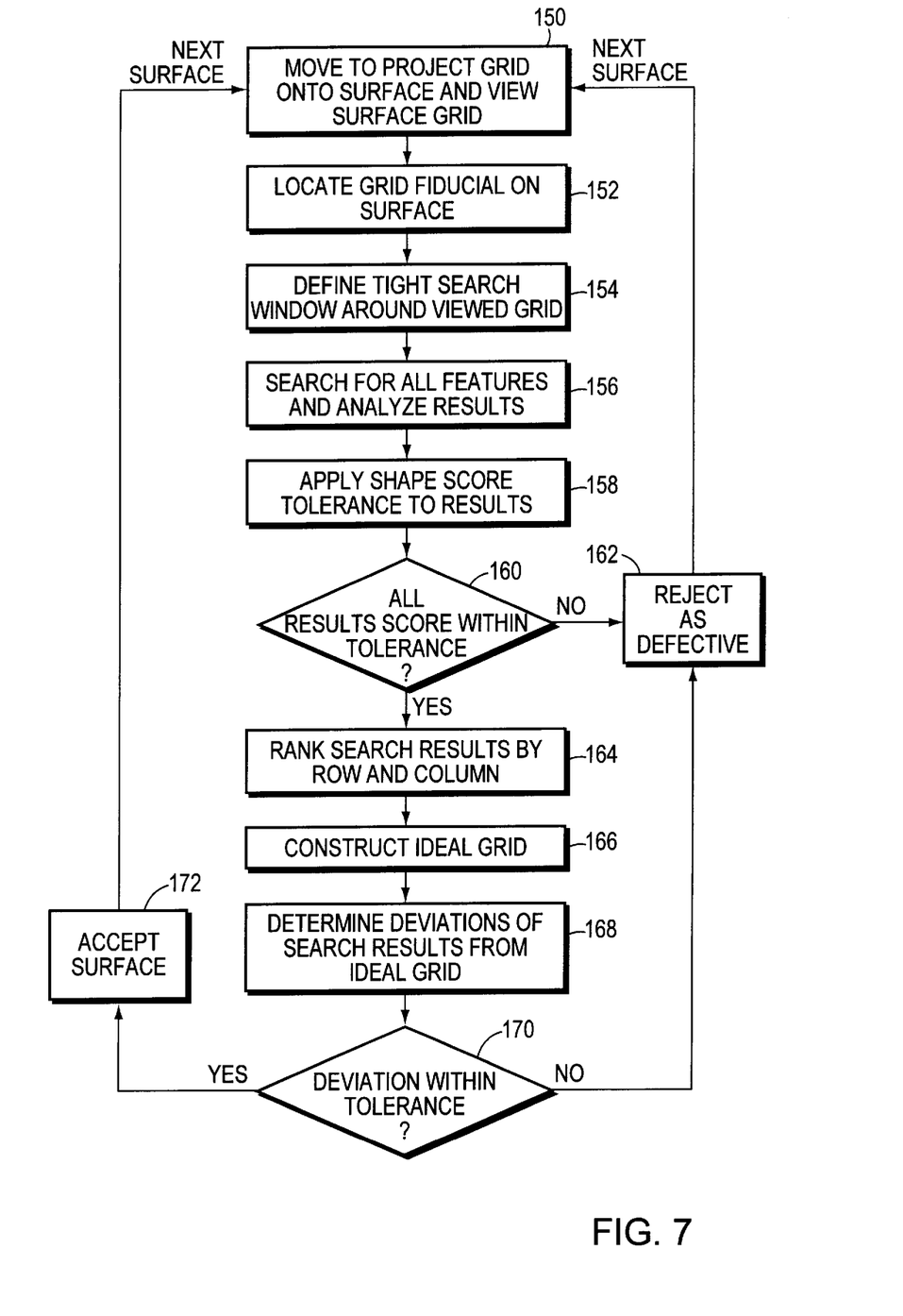
FIG. 7 is a flow diagram of a technique according to this invention for analyzing grid features produced using the structured illuminator.

FIG. 7 describes a technique according to this invention, according to this invention, for inspecting surfaces based upon the preferred illumination pattern. Two discrete steps for analyzing the viewed grid are used. In general, these two steps each entail the quantification of defects in the surface based upon the viewed grid. These techniques are not completely independent of each other, but they do employ different interpretations of the grid image information acquired by the machine vision system via the camera to perform the desired quantification of defects. Based upon the use of these two techniques, to be described in detail below, a reasonably high degree of defect identification/quantification is attained.

First, the surface and/or inspection device (including the illuminator and camera) is moved so that the grid, including the reference fiducial, is projected on the surface at an appropriate location as denoted the grid is projected on the surface at an appropriate location (as denoted by block 150 of FIG. 7), and as described in detail above. Next, the grid's reference fiducial is located on the surface (block 152). According to one embodiment, the PatMax/Align pattern-recognition software tool, commercially available from Cognex Corporation of Natick, Mass., can be utilized to locate the fiducial and to lay down a corresponding region of interest with respect to the fiducial. In general, a region is established to tightly encompass the area of the grid lattice itself (block 154). In the referred grid arrangement of this invention thirty-six intersecting grid lines are surrounded by this region. These intersecting grid lines are then located using pattern-matching—which can be performed using the PatMax/Align software tool, or any other acceptable object location/identification machine vision tool including a conventional normalized correlation technique.

After locating the grid, and then searching out and identifying the discrete features therein (squares in this embodiment, circles an alternate embodiment (see FIG. 3)), the system scores each feature (block 156). Scoring can be based upon a variety of criteria or parameters. For example, the system can be preloaded with data that instructs it to search for square shapes and compare them to "perfect squares." The variation from perfect is then quantified based upon a preset scale to generate a percentage score.

For the purposes of this embodiment, PatMax/Align, or another advanced machine-vision technique, is preferred because it enables accurate recognition and scoring of shapes even in the presence of scale variation. In particular, when the viewed surface is disposed at a non-perpendicular angle with respect to the camera axis, the grid features along one orthogonal axis will appear to have a different spacing than the features taken along the other axis. In this case, the scores of the shapes (grid squares in this embodiment) returned by a standard pattern-matching algorithm (such as normalized correlation) would be less than one hundred percent. This is because these algorithms return a shape score by undertaking a gray scale pixel-by-pixel comparison of preloaded model data (previously taken from a sample object image) to that of an actual viewed image, and by then grading the resulting comparison based upon the coverage of the matching pixels. Conversely, an advanced algorithm (for example, the PatMax Align tool) has features such as scale invariance, which can compensate for uniform distortion, thereby scoring such shapes at one hundred percent by identifying the scale variation of the grid features. Lacking the flexibility of PatMax/Align and similarly advanced machine vision tools, the surface must be maintained essentially flat and perpendicular to the camera axis during analysis in order to achieve perfect shape scoring.

In addition, the PatMax/Align tool contains elasticity features that enable ready identification of non-uniformly distorted features. This is particularly useful where the reference fiducial is placed over a defect, and may, itself, appear distorted.

The Pat/Max/Align tool, when analyzing each viewed grid feature, returns the desired shape score. Each shape score is then compared to a minimum tolerance value (blocks 158 and 160) the minimum tolerance level is based upon the level of defect that is acceptable. For example, if only large defects are sought, a score tolerance set to fail at only seventy percent may be sufficient, whereas a more-restrictive tolerance set to fail at eighty-five percent may be necessary for detection of smaller defects. If a given surface contains features having shape scores lying outside tolerance limits then the surface is rejected as defective (block 162), and the next surface is viewed (block 150).

Figure 8:
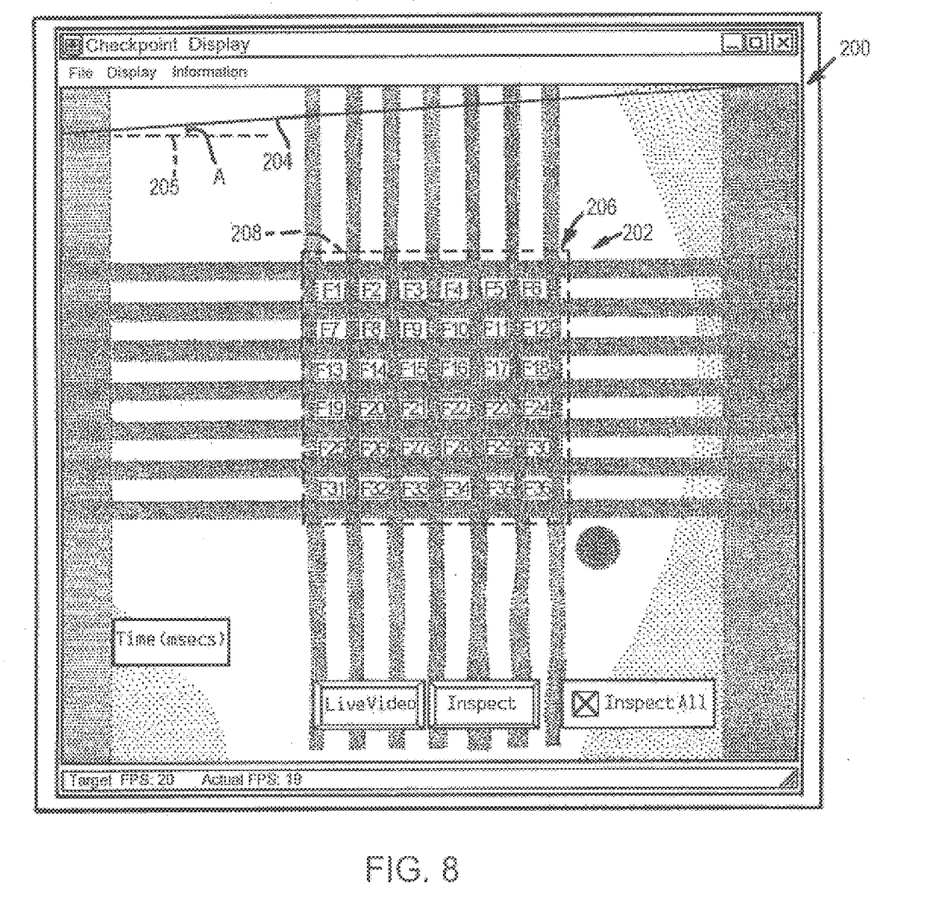
FIG. 8 is a plan view of viewed image of a grid pattern on a defective surface further detailing the ranking of grid features and derivation of an ideal grid in accordance with FIG. 7.

Alternatively, if the surface meets acceptable tolerance limits, then the surface can be considered acceptable for the first step of the analysis. The second step of the analysis entails the calculation of positional errors within the viewed grid. The located features from block 156 are now ranked according to row and column (block 164). Reference is made generally to the representative machine-vision-system computer display 200, showing the viewed grid 202. In particular such ranking can be accomplished by defining a line 204 slope having an angle A of between approximately 5° to 15° from the horizontal (dotted line 205) and located above the grid (e.g. a non-parallel line to each orthogonal grid axis). The relative distance from the line is used to establish a positional ranking of the grid features. The specific ranking of the illustrated square grid features is denoted in ranked order by reference numbers F1–F36.

Based upon the ranking, an ideal grid can be constructed for comparison with the actual viewed grid. Construction of an ideal grid is desirable because slight variations in the texture of the surface inspected or its curvature and/or slope can cause significant global changes in grid size and position. Such global variations should not be considered defects and, thus, should be accounted for by the inspection process. The construction of the ideal grid is referenced in block 166. The six-by-six grid pattern of the preferred embodiment is constructed as an ideal grid by using the mean positions of the located features on boundaries (dotted lines 206) of the grid. For example the top boundary 208 of the grid would be defined as the average of the six top-most feature (F1–F6) locations. In other words, the top boundary 208 is a horizontal line best fitting features F1–F6. Once an ideal grid is constructed deviation of located features from their ideal grid locations is computed (block 168). Each location has associated therewith a tolerance value representing maximum deviation from the ideal location. In general, sensitivity to defects increases as the tolerance decreases. The magnitude of the deviation depends generally upon the quality of the defect. By way of example, defects with very rapid changes in height typically cause large distortions. Similarly, the magnitude of the tolerance applied depends upon the quality of the worst allowable defect. A larger tolerance should be applied where larger defects are acceptable. In the particular example of inspecting Smart Cards, in this embodiment, the tolerance of the grid pattern is set to a deviation of approximately 2.5 pixels—that is, if an actual grid feature location deviates from an ideal location by a viewed amount of more than 2.5 pixels within an image frame then a defect is indicated. According to the decision block 170, if all deviations are within the predefined tolerance range, then the surface is accepted (block 172), and the next surface is set up for inspection. Conversely, if one or more deviations are out of tolerance, then the surface is rejected (block 162), and the next surface is inspected.

Another advantage of using an advanced pattern recognition tool such as PatMax/Align is the ability to locate grid features to within an accuracy of approximately $1/40^{th}$ of a pixel versus the ¼ pixel accuracy of more-conventional alignment processes. This translates into a grid accuracy variation of approximately one percent, for such a tool, compared with about ten percent with normalized correlation—given that the prevailing tolerance according to this embodiment is approximately 2.5 pixels.

The foregoing has been a detailed description of a preferred embodiment of the invention. Various modifications and additions can be made without departing from the spirit and scope of the invention. For example, the term "grid" as used herein should be taken broadly to include a variety of different grid feature shapes that define intersecting or touching features. Circular features can be used according to different embodiments or a combination of different grid patterns can be used at the same time. Grids can be spread out along rectilinear vertical/horizontal axes, or according to different orientation rules. Also, while the projecting element of the illumination assembly defines a rectangular box as detailed herein, a variety of structured illumination techniques can be substituted according to alternate embodiments. Likewise, while a scoring and positional analysis is used to locate defects according to this description, it is contemplated that the analysis techniques used herein to determine defects can be modified, or in the alternative, combined with other techniques. Accordingly, this description is meant to be taken only by way of example, and not to otherwise limit the scope of the invention.

What is claimed is:

1. A system for inspecting a surface comprising:
    a structured illuminator that projects a predetermined grid pattern having a plurality of grid features on the surface;
    a camera arranged to view the arid pattern;
    a machine vision processor constructed and arranged to compare a score of each of the grid features and a location of each of the grid features against predetermined limitations to thereby determine whether the grid features exceed the limitations; and
    wherein the machine vision processor is further constructed and arranged to (a) determine a respective score for each of the features based upon predetermined scoring parameters; (b) determine actual locations of each of the grid features viewed; (c) construct ideal locations for ideal grid features, (d) compare each score against a desired tolerance; and (e) compare each of the actual locations against the ideal grid features.

2. The system as set forth in claim 1 wherein the grid features viewed are arranged in a plurality of rows and columns and the machine vision processor is constructed and arranged to construct the ideal locations by ranking each of the grid features viewed with respect to the rows and columns and to define the ideal grid locations with respect to the rows and columns.

3. The system as set forth in claim 2 wherein the ideal grid locations are defined based upon predetermined distances between the ideal grid locations and a line disposed at a non-parallel angle with respect to each of the rows and columns.

4. The system as set forth in claim 1 wherein the structured illuminator includes a projecting element that includes a diffuser assembly for receiving light from the source and a grid for defining the grid pattern through which the light passes and a beam splitter that reflects at least a portion of the light received from the grid at a right angle toward the surface and having an open top above the beam splitter constructed and arranged so that light transmitted from the surface through the beam splitter to the camera in line with a viewing axis of the camera, the viewing axis being substantially perpendicular to the surface.

5. The system as set forth in claim 4 wherein the illuminator includes a first polarizer located between the diffuser assembly and the grid and a second polarizer positioned over the camera.

6. The system as set forth in claim 5 further comprising a collimator located between the diffuser assembly and the grid.

7. The system as set forth in claim 6 wherein the camera includes a telecentric lens.

8. A method for inspecting a surface comprising:

projecting a predetermined arid pattern having a plurality of grid features on the surface;

viewing the grid pattern with a camera arranged on a viewing axis with respect to the surface;

comparing, with a machine vision processor, a score of each of the grid features and a location of each of the grid features against predetermined limitations to thereby determining whether the grid features exceed the limitations; and wherein the step of comparing the score of each of the grid features further includes (a) determining a respective score for each of the features based upon predetermined scoring parameters; (b) determining actual locations of each of the grid features viewed; (c) constructing ideal locations for ideal grid features; (d) comparing each score against a desired tolerance and (e) comparing each of the actual locations against the ideal grid features.

9. The method as set forth in claim 8 further comprising defining a plurality of rows and columns with respect to the grid pattern and constructing the ideal locations by ranking each of the grid features viewed with respect to the rows and columns and defining the ideal grid locations with respect to the rows and columns.

10. The method as set forth in claim 9 wherein the step of defining the ideal grid locations includes establishing a line disposed at a non-parallel angle with respect to each of the rows and columns and applying predetermined distances between the ideal grid locations the line.

11. The method as set forth in claim 8 wherein the step of projecting includes transmitting a light through a structured illuminator having a projecting element that includes a diffuser assembly for receiving light from the source and a grid for defining the grid pattern through which the light passes and a bean splitter that reflects at least a portion of the light received from the grid at a right angle toward the surface and receiving light having the grid pattern defined thereon from the surface through an open top above the beam splitter at the camera in line with the viewing axis of the camera, the viewing axis being substantially perpendicular to the surface.

12. The method as set forth in claim 11 further comprising positioning a first polarizer between the diffuser assembly and the grid and a positioning a second polarizer over the camera.

13. The method as set forth in claim 12 further comprising positioning a collimator between the diffuser assembly and the grid.

* * * * *

UNITED STATES PATENT AND TRADEMARK OFFICE
CERTIFICATE OF CORRECTION

PATENT NO. : 6,191,850 B1
DATED : February 20, 2001
INVENTOR(S) : Gilbert W. J. Chiang Page 1 of 1

It is certified that error appears in the above-identified patent and that said Letters Patent is hereby corrected as shown below:

Column 8,
Line 24 (claim 1, line 5), replace "arid" with -- grid --.

Column 9,
Line 4 (claim 8, line 2), replace "arid" with -- grid --.

Column 10,
Line 11 (claim 11, line 6), replace "bean" with -- beam --.

Signed and Sealed this

Thirteenth Day of November, 2001

Attest:

*Attesting Officer*

NICHOLAS P. GODICI
*Acting Director of the United States Patent and Trademark Office*